United States Patent [19]

Kraus

[11] 4,195,026
[45] Mar. 25, 1980

[54] SUBSTITUTED FURANS FROM BUTENOLIDES

[75] Inventor: George A. Kraus, Ames, Iowa

[73] Assignee: Iowa State University Research Foundation, Inc., Ames, Iowa

[21] Appl. No.: 966,268

[22] Filed: Dec. 4, 1978

[51] Int. Cl.$^2$ .................. C07D 307/36; C07D 307/58
[52] U.S. Cl. ............................ 260/346.11; 260/347.2; 260/347.4; 260/347.5; 260/347.8
[58] Field of Search .............. 260/347.8, 347.4, 347.2, 260/346.11, 347.5

[56] References Cited
U.S. PATENT DOCUMENTS 3,113,939  12/1963  Martin .......................... 260/347.8 X

*Primary Examiner*—Richard Raymond
*Attorney, Agent, or Firm*—Zarley, McKee, Thomte, Voorhees & Sease

[57] ABSTRACT

A method of preparing alkoxy and acyloxy furans from butenolides comprising reacting a butenolide with an alkylating agent in the presence of a base to provide an alkylated or acylated furan ring containing intermediate, which in turn is reacted under metallating conditions with an organic electrophile to provide addition of the electrophile to the gamma position of the furan ring. Under the conditions of the reaction, it has been discovered that the butenolide ring will undergo rearrangement to provide the furan ring, forming the nucleus for synthesis of a wide variety of furan compounds.

12 Claims, No Drawings

SUBSTITUTED FURANS FROM BUTENOLIDES

GRANT REFERENCE

The invention described herein was made in the course of work under a grant or award from the Department of Health, Education and Welfare.

BACKGROUND OF THE INVENTION

This invention relates to preparation of substituted alkoxy and acyloxy furans using as starting materials butenolides. Prior to this invention there has been no reasonable synthetic method for the general preparation of alkoxy furans or acyloxy furans. Often such compounds have been painstakingly and meticulously isolated from natural sources. This is very expensive, time consuming and does not provide significant product yields.

As those skilled in the art know and understand, furan compounds are those which contain at some point in the compound's structure the following common nucleus:

Such furan ring containing compounds are valuable presursors for the preparation of a wide variety of biologically active compounds. They can, for example, be successfully used as the starting point for preparation of complex butenolides, of other substituted furans, and they can be used for the making of such biologically active compounds, such as lycorine which is an antibacterial agent whose structure represents a challenge to present methods of synthesis, gibberelic acid, which is an important plant growth regulator that is not easily available from natural sources, and protoanemonin and its substituted derivatives, among others. In short, the number of desirable biologically active compounds which can be prepared using as a nucleus the furan moiety, is almost limitless. However, the effective utilization of furans as a precursor for preparation the numerous desirable biologically active compounds such as those listed above has met with only limited success and usage in the past. This is so primarily because of the difficulty of obtaining the furan starting materials.

Accordingly, the primary object of this invention is to provide a synthesis process which allows for quick, easy, high yield preparation of furan compounds.

Another object of this invention is to provide a synthetic process for furans which in turn can be used as building blocks for preparing a wide variety of biologically active compounds.

Yet another object of this invention is to provide a synthetic process for furans which uses readily available butenolides as a starting material, which under the conditions of the reactions of this invention, undergo rearrangement to the furan ring.

An even further object of this invention is to provide a process of alkylating butenolides to provide an alkylated furan intermediate which will quickly and easily add an electrophilic agent, under metallating conditions to provide a substituted furan.

The method and manner of accomplishing these objects of this invention, as well as others, will become apparent from the detailed description of the invention, which follows.

SUMMARY OF THE INVENTION

A butenolide or substituted butenolide wherein the substituted moiety is a non-functionally substituted alkyl, alkenyl, alkynyl, or an aryl is reacted with an alkylating agent, such as a trialkyl chlorosilane, in the presence of a base and a suitable organic solvent, to provide an alkylated furan ring containing intermediate. The intermediate in turn is reacted under metallating conditions with an organic electrophile to provide addition of the electrophile to the furan ring at a position which corresponds to the gamma position of the original butenolide ring.

DETAILED DESCRIPTION OF THE INVENTION

In accordance with the first step of the process of this invention, a butenolide of the following formula is the starting material:

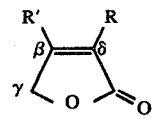

As can be seen, the starting butenolide may if desired be substituted at the alpha and beta position. It cannot, however, be substituted at the gamma position since after the subsequently described rearrangement to a furan, the electrophile is added at the gamma position of the starting butenolide.

R and R' can be selected from the group consisting of hydrogen, and nonfunctionally substituted alkyls, alkenyls, alknyls and aryls. The R and R' moieties must be non-functionally substituted in order to prevent undesired side reactions from occurring on these side chain moieties, as opposed to undergoing the desired furan rearrangement. For example, it has been found that if either R or R' is substituted with the carbomethoxy group, the reaction fails. Preferably R and R' are $C_1$ to $C_{12}$ substituents.

The butenolide in the first step reaction is reacted with an alkylating agent which must be a trialkyl halosilane alkylating agent of the following formula:

X represents any halide. It is, however, most preferably chloride. A, B and C represent alkyl groups, preferably $C_1$ to $C_{12}$ alkyl groups either straight or branched chain. The most preferred trialkyl halosilane alkylating agent is butyl dimethylchlorosilane in which A and C are dimethyl groups and B represents tertiarybutyl group. Tertiary butyldimethylchlorosilane is the most preferred alkylating agent because of easy availability and the good results achieved when it is used as the alkylating agent.

The butenolide and the alkylating agent are reacted together in the presence of a base and a substantially inert solvent. The solvent maybe any anhydrous inert solvent such as ether and tetrahydrofuran or dimethoxyethane, commonly referred to as glyme. The purpose of the base is to remove a proton from the gamma position of butenolide ring. Suitable bases are well known and the work-up for such bases is well known in the art. Bases which will work in the reaction of this invention are preferably the dialkylamide bases which are formed by the reaction of alkyl lithiums and dialkyl amines. Preferably the alkyl group is $C_2$ or greater. For example, tertiarybutyllithium with a compound such as disopropyl amine may be dissolved in tetrohydrofuran (THF) and hexamethylphosphoric triamide (HMPA) to provide a base such as di-isopropyl lithium amide represented by the following formula:

i-Pr$_2$N Li

Preparation of the bases suitable for reaction in this invention is well known and will not be described in detail. For further reference to the preparation of bases, see for example J. American Chemical Society, 89 (1967) at pages 2500 through 2503 which is incorporated herein by reference.

Since the reaction ingredients for this reaction are highly reactive, it is preferable, and in most cases essential that the reaction be conducted in an inert atmosphere such as an argon or nitrogen atmosphere. Any oxygen which is present will react with the base and the intermediate carbanion which is formed. It is for this reason that the system is flushed with an inert gas.

The reaction of the butenolide and the preferred trialkylchlorosilane alkylating agent, in the presence of a base will provide addition of the alkylating agent on the butenolide ring and rearrangement to a furan ring. The resulting intermediate compound has the following formula.

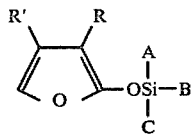

It has been found most desirable and efficient when equimolar quantities of all reactants are employed. Reaction temperatures likewise are not critical, although it has been found desirable to react at room temperature, or lower. Pressure does not appear to be a controlling factor. Atmospheric pressure works satisfactorily.

As can be seen from the structural formula presented for the alkylated compound, there is a rearrangement from the butenolide ring formation in the initial starting reactant to the furan ring arrangement. The intermediate alkylated compound is next reacted, under metallating conditions, with an organic electrophile in order to add the organic electrophilic agent to the furan ring at the gamma position.

Again, metallating conditions are well known to those skilled in the art of organic synthesis and need not be detailed herein any further than is specifically detailed in the examples. However, basically the metallation is accomplished by reacting the desired organic electrophilic agent with the intermediate alkylated compound in the presence of an alkyl lithium compound. A suitable alkyl lithium compound is tertiarybutyllithium. Preferably the reaction is conducted in the presence of ether.

In the metallating reaction wherein the trialkyl silyl substituted furan is reacted with an organic electrophilic reagent, the suitable electrophile is almost limitless. It can be any preselected organic compound which is desired for addition at the gamma position of the furan ring. The exact electrophile used will, of course, depend upon the furan which one is synthesizing. The reaction can be represented by the following formula:

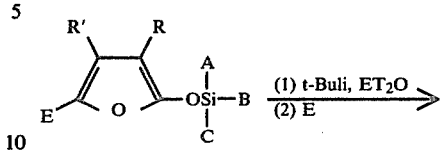

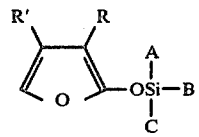

In the above reaction the electrophile is represented by E.

The suitable electrophilic agents and conditions for the reaction are specified in the examples below. There is no criticality to reaction conditions, but generally it is preferred that the equal molar quantities of the reactants be employed, that the reaction be conducted under an inert atmosphere, and that ambient temperatures or sub-ambient conditions be employed. Atmospheric pressure is very satisfactory.

As heretofore mentioned, there is no criticality with regard to the electrophilic addition compound being used, its precise structure being chosen by the desired structure selected for addition to the furan ring. Generally, however, both substituted and unsubstituted, straight chain, branched chain and cyclic compounds may be used as well as aromatics, both substituted and unsubstituted. Examples of suitable electrophiles include: disulphides, alkylhalides, aldehydes, ketones, acid chlorides, halosilanes, and epoxides. After the electrophilic agent has been added to metallated furan, the silane moiety may be removed if desired by the addition of a dilute aqueous acid such as p-toluene sulfonic acid in aqueous THF. Such removal reactions again are likewise well known and for a general description thereof see J. American Chem. Soc. 94, (1972) at pages 6190 through 6192 which are incorporated herein by reference. The removal procedure is also explained further in the examples.

The following samples will serve to illustrate the synthesis and scope of the invention but are not intended as limiting.

EXAMPLES 1 THROUGH 9

In each of the following examples butenolide was reacted with an alkylating agent which comprised a trialkylchlorosilane, namely, dimethyl tertiary butyl-chlorosilane in tetrahydrofuran solvent in the presence of i-Pr$_2$N base and hexamethyl phosphoric triamide to provide an 85% yield of an intermediate furan oxy silane of the formula:

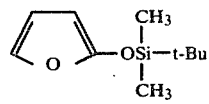

The equation for the reaction is as follows:

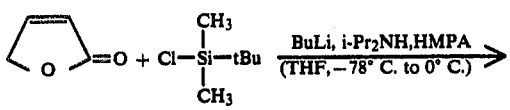

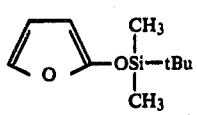

The amounts of each ingredient were equal molar amounts and are listed in Table I below. The reaction was run at atmospheric pressure, under a nitrogen atmosphere. Cooling of the reaction ingredients was by a dry ice-acetone bath.

TABLE I

| Δ | Butenolide | BuLi | i-Pr₂NH | HMPA | tert-Butyl, dimethyl silyloxy furan. |
|---|---|---|---|---|---|
| MW | 84 | 2.45W | 101 | 179 | 151 |
| GMS | 1.0 | | 1.44 | 2.33 | 2.0 |
| Ml | | 5.31 | 2.00 | 2.26 | |
| Moles | 12 | 13 | 14.3 | 13 | 13.2 |

The reaction was conducted at −78° C. initially and allowed to gradually warm to 0° C. The ingredients were added in the following manner. The butenolide was added to the tetrahydrofuran solvent which in turn was added to the Lithium-diisopropyl-amide-HMPA complex at −78° C. over a ten minute period. Stirring continued for 20 minutes and then the tertiary butyl-dimethylchlorosilane alkylating agent was added rapidly. Stirring continued for an additional ten minutes at −78° C. and then for an additional 60 minutes at 0° C. After the 60 minutes of continual stirring at 0° C., the reaction mixture was poured into approximately 200 milliliters of hexane. The organic layer which separated was washed twice with 50 milliliters of water and once with a 25 milliliter of brine solution, followed by drying with sodium sulfate. It was thereafter filtered and roto-evaporated. Chromotography analysis was conducted to reveal an 85% yield of the desired furan ring containing compound.

Thereafter, the separated intermediate was utilized in the second step reaction procedure for reacting with an electrophile in the presence of a metallating agent to provide the substituted furan.

The amount of each ingredient was in accordance with Table II below. The product of Example 1 is a substituted analog of protonanemonin, which is known to possess physiological activity according to J. Med. Chemistry, 11, 1176.

| Ex. | Amount of Alkylated Intermediate | t-BuLi | E | Amount of E | Furan Product | Yield |
|---|---|---|---|---|---|---|
| 1. | 1.082 gms | .36ml. | 6-methyl-5-heptene-2-one | 0.5 gms | 1.11 gms | 70% |
| 2. | 0.99 | 3.3 | Ph—C(=O)—H | .600 | .97 gms | 61% |
| 3. | 0.99 | 3.3 | Pr—C(=O)—H | .38 | .62 | 45% |
| 4. | 0.99 | 3.3 | CH₃—CH=CH—C(H)=C(CHO)(H) | .50 | .65 | 44% |
| 5. | 0.99 | 3.3 | (cyclohexene with OSiEt₃, C(=O)CH₃, CH₃, CH₃ substituents) | 1.55 | 2.06 | 81% |
| 6. | 0.99 | 3.3 | ClCO₂Et | .53 | .94 | 70% |
| 7. | 0.99 | 3.3 | Ph—S—S—Ph | 1.09 | 1.22 | 80% |
| 8. | 0.99 | 3.3 | CH₃I | .75 | .69 | 65% |
| 9. | 0.99 | 3.3 | ClSi(CH₃)₃ | .61 | 1.24 | 92% |

In conducting the second step reaction the procedure was as follows: The tertiary butyllithium was added to the tertiary butyl dimethylsiloxyfuran at −50° C. It was allowed to warm to −40° C. and then stirred for 60 minutes. Thereafter, it was cooled to −60° C. and the electrophile, dissolved in ether was added. It was allowed to warm slowly to 0° C. and then quenched with one normal hydrocholoric acid. The dilute ether layer was washed once with 15 milliliters of one normal hydrochloric acid, and once with a brine solution. It was thereafter dried with sodium sulfate, filtered and roto-evaporated. Chromatographic analysis of the product was then conducted in order to determine the percent yield of the desired furan product. Percents are reported in Table II under the heading "Yield".

As can be seen, complex furan products have been provided at the lowest yield level of 44% and at the highest yield level (see example 9) of 92%. Thus, the invention has provided for a simple effective synthetic route for converting butenolide compounds to complex furans. Moreover, the reaction is a simple two-step reaction with a minimum of complex procedures involved.

What is claimed is:

1. A method of preparing gamma position substituted furans from a butenolide comprising, reacting a butenolide of the formula:

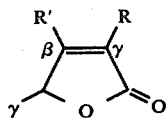

wherein R and R' are selected from the group consisting of hydrogen and non-functionally substituted alkyls, alkenyls, alkynyls and aryls with a trialkyl chlorosilane alkylating agent in the presence of a strong organic base and a suitable organic solvent for said base to provide a silane moiety alkylated furan ring containing intermediate; and thereafter reacting said furan ring containing intermediate, under metallating conditions, with an organic electrophile to provide addition of said electrophile to the gamma position of said furan ring; and thereafter removing the silane moiety from said ring to provide a gamma substituted furan.

2. The process of claim 1 wherein R and R' are $C_1$ to $C_{12}$ substituents.

3. The process of claim 1 wherein said trialkyl chlorosilane is a $C_1$ to $C_{12}$ trialkyl compound.

4. The process of claim 1 wherein said strong organic base is a dialkylamide base.

5. The process of claim 1 which is conducted in an inert atmosphere.

6. The process of claim 1 wherein the process is conducted in an inert solvent.

7. The process of claim 4 wherein said dialkyl moiety of said dialkylamide is $C_2$ or greater.

8. The process of claim 1 wherein substantially equimolar quantities of the reactants are employed.

9. The process of claim 1 wherein the electrophile is selected from the group consisting of organic disulphides, alkyhalides, aldehydes, ketones, acid chlorides, halosilanes and epoxides.

10. The process of claim 1 wherein said reaction is conducted at temperatures within the range of $-78°$ to $0°$ C.

11. The process of claim 1 wherein removal of said silane moiety is by addition of a dilute acid.

12. A method of preparing gamma position substituted silyloxy furans from a butenolide comprising, reacting a butenolide of the formula:

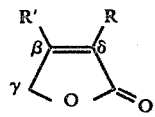

wherein R and R' are selected from the group consisting of hydrogen and non-functionally substituted alkyls, alkenyls, alkynyls and aryls with a trialkyl chlorosilane alkylating agent in the presence of a strong organic base and a suitable organic solvent for said base to provide a silane moiety, alkylated furan ring containing intermediate; and thereafter reacting said furan ring containing intermediate, under metallating conditions, with an organic electrophile to provide addition of said electrophile to the gamma position of said furan ring.

* * * * *